United States Patent [19]
Brown

[11] Patent Number: 6,074,657
[45] Date of Patent: *Jun. 13, 2000

[54] ADMINISTRATION OF AN INJECTABLE ANTIBIOTIC IN THE EAR OF AN ANIMAL

[75] Inventor: Scott A. Brown, Galesburg, Mich.

[73] Assignee: Pharmacia & Upjohn Company

[ * ] Notice: This patent issued on a continued prosecution application filed under 37 CFR 1.53(d), and is subject to the twenty year patent term provisions of 35 U.S.C. 154(a)(2).

[21] Appl. No.: 08/822,195

[22] Filed: Mar. 20, 1997

[51] Int. Cl.$^7$ ...................................................... A61F 2/02
[52] U.S. Cl. ............................................................. 424/423
[58] Field of Search ................................................ 424/423

[56] References Cited

U.S. PATENT DOCUMENTS

| | | |
|---|---|---|
| 3,428,729 | 2/1969 | Anderson et al. . |
| 4,464,367 | 8/1984 | Labeeuw et al. . |
| 4,495,898 | 1/1985 | Akhavein et al. . |
| 4,506,630 | 3/1985 | Hair . |
| 4,631,231 | 12/1986 | Stendel et al. . |
| 4,902,683 | 2/1990 | Amin et al. . |
| 5,079,007 | 1/1992 | Putnam . |

FOREIGN PATENT DOCUMENTS

| | | |
|---|---|---|
| 2239-988 | 11/1975 | France . |
| 59-181208 | 10/1984 | Japan . |
| 889601 | 12/1988 | South Africa . |
| WO 94/20505 | 9/1994 | WIPO . |
| WO 96/40351 | 12/1996 | WIPO . |

OTHER PUBLICATIONS

"Microchip Implant Sites Identified by USDA," Feedstuffs, p. 6, Sep. 30, 1996.
Watson, TG, et al.; New Zealand Veterinary Journal, 42(2):67–69 (1995).
McHardy, M. and Morgan, DWT; Research in Veterinary Science, 39:1–4 (1985).
Houpert, P., et al.; Veterinary Research, 24:278–285 (1993).
*Bilalov, FB, Diagnosis of Infectious Diseases of Farm Animals, pp. 132–135 (1982)—Russian Language.
*Rumachik, I., et al. Veterinarnaya Nauka–Proizvodstvu, 26:36–44 (1988)—Russian Language.
Genov, I., et al.; Veterinarnomeditsinski nauki, 47(2):42–47 (1980). English Translation provided.
McKercher, PD and Bachrach, HL; Can. J. Comp. Med., 40(1):67–74 (1976).
Alogninouwa, Th., et al.; Revue Med. Vet., 144(7):599–604 (1993). English Translation provided.
Koutchoukali, M.A., et al.; Revue de Medecine Veterinarie, 136(7):505–508 (1985). English Translation provided.
Toma, B., et al.; Recueil de Medecine Veterinaire, 159(7):645–652 (1983). English Translation provided.
Borgman, RF, et al.; American Journal of Veterinary Research, 33(11):2309–2315 (1972).

*Primary Examiner*—Carlos Azpuru
*Attorney, Agent, or Firm*—Martha A. Gammill

[57] ABSTRACT

The present invention provides for a method of injecting an antibiotic in the ear of an animal, such as cattle, swine, sheep and goats. These injectable antibiotics include the following: injectable suspensions of sparingly water-soluble antimicrobial agents, such as procaine penicillin, benzathine penicillin, ceftiofur crystalline free acid ceftiofur hydrochloride, ampicillin trihydrate and amoxicillin trihydrate; sustained-release non-aqueous solutions of sparingly water-soluble antimicrobial agents, such as oxytetracycline, erythromycin, tylosin, tilmicosin and florfenicol; and injectable solutions of zwitterionic antimicrobial agents, such as enrofloxacin, danofloxacin and premafloxacin. Specifically, the present invention provides for a method of injecting a relatively large volume (1 to 15 mL) of a sterile oil suspension of an antibiotic, such as ceftiofur crystalline free acid, in the posterior of the ear of cattle and swine.

16 Claims, 1 Drawing Sheet

ADMINISTRATION OF AN INJECTABLE ANTIBIOTIC IN THE EAR OF AN ANIMAL

FIELD OF THE INVENTION

The present invention provides for a method of injecting an antibiotic in the ear of an animal, such as cattle, swine, sheep and goats. These injectable antibiotics include the following: injectable suspensions of sparingly water-soluble antimicrobial agents, such as procaine penicillin, benzathine penicillin, ceftiofur crystalline free acid, ampicillin trihydrate and amoxicillin trihydrate; sustained-release non-aqueous solutions of sparingly water-soluble antimicrobial agents, such as oxytetracycline, erythromycin, tylosin, tilmicosin and florfenicol; and injectable solutions of zwitterionic antimicrobial agents, such as enrofloxacin, danofloxacin and premafloxacin. Specifically, the present invention provides for a method of injecting a relatively large volume (1 to 15 mL) of a sterile oil suspension of an antibiotic, such as ceftiofur crystalline free acid of formula I, in the posterior of the ear of cattle and swine.

BACKGROUND OF THE INVENTION

The injection of many antibiotics produces irritation and, potentially, illegal drug residues at the injection site of food-producing animals. Current cattle practice is oriented toward changing from an intramuscular injection of drugs and vaccines, which then leaves both irritation and possibly drug residues in edible meat, to subcutaneous injection, which places those unwanted occurrences at the surface of the carcass in cattle. Because the hide of cattle is removed at slaughter, the injection sites are potentially visible and will be trimmed from the carcass. Even if that is not done, the edible meat is not damaged because the injection is not into muscle. Nevertheless, even with subcutaneous administration, injection site irritation and potentially violative drug residues still remain on an edible portion of the carcass, namely the surface of the carcass itself.

Furthermore, any violative drug residues at the injection site cannot be monitored by current United States Department of Agriculture (USDA) inspectors, who require a "target tissue" for residue monitoring to homogeneously contain drug residues and always be readily identifiable to the layman. These target tissues are now defined as the kidney, liver, muscle and fat; and an injection site in any edible tissue, regardless of whether the injection is intramuscular or subcutaneous, fails the criteria for a target tissue because it is not always readily identifiable, circumscript or homogenous with respect to drug residues.

The only alternative for antibiotics which have injection site residues, that are unacceptable as target tissues, is to use surrogate target tissue with which to monitor residue depletion. In that case, the surrogate target tissue is not the tissue in which potentially unsafe residues reside, but rather is the circumscript and/or homogeneous tissue (with respect to incurred drug residues) for which residues can be monitored until the time after drug administration at which all other drug residues in tissues decrease to safe levels. Because it is a surrogate target tissue, residues must decrease to a much lower concentration than those determined to be safe for that tissue from toxicological studies and food consumption values, in essence, penalizing that tissue's safe concentration because it is being used as a surrogate for the injection site.

Ceftiofur crystalline free acid sterile oil suspension (CCFA-SS), which will be described further below, is a sustained-release ceftiofur product under development that provides for prolonged absorption from the injection site and thus affords a single injection treatment of bacterial diseases in animals. The prolonged absorption of the drug from the injection site makes the injection site contain the highest concentration of drug residues for the longest period of time (several weeks) during which time the concentration in all other tissues decreases to non-detectable levels. This makes the use of a surrogate target tissue impossible for this antibiotic.

This is not unique to ceftiofur crystalline free acid, but rather is common to all sustained-release injectable compounds. Heretofore, the only alternative has been to utilize the surrogate tissue approach described above, as a result of injection site residues remaining with the edible carcass of food-producing animals.

Therefore, what is needed in the art is a way to administer to food-producing animals therapeutic agents, and specifically, antibacterial agents such as ceftiofur crystalline free acid, which satisfies the applicable regulatory and consumer health requirements regarding human food safety. In accordance with the present invention, this may be achieved by removing prolonged drug residues from the edible tissues of the food-producing animal, and yet provide the food-animal producer with products that offer the convenience of sustained-delivery injectable systems, that have slaughter withdrawal periods that optimize the return on their investment and that have use flexibility in the field situation.

International Publication No. WO 94/20505, published Sept. 15, 1994, discloses ceftiofur crystalline free acid, its preparation and its method of administration. In the examples in that publication, it states that cattle were administered ceftiofur crystalline free acid by injection intramuscularly or subcutaneously either in or on the edible tissues of the animals. At page 10 of the publication it refers to antibiotics implants disclosed in U.S. Pat. No. 5,079,007 and to various pharmaceutical dosage forms exemplified in U.S. Pat. No. 4,902,683.

Putnam, Controlled Release of Antibiotic Salts from an Implant, U.S. Pat. No. 5,079,007, Jan. 7, 1992, discloses a formulation, in pellet or tablet form, providing for the controlled release implant of a cephalosporin antibiotic, particularly ceftiofur, consisting of: (a) a crystalline salt of the cephalosporin, particularly ceftiofur hydrochloride; (b) an amorphous salt of the cephalosporin, particularly ceftiofur sodium; and (c) excipients. It only discloses intramuscular implantation as the preferred route of administration.

Amin et al., Crystalline Cephalosporin Hydrohalide Salts, U.S. Pat. No. 4,902,683, Feb. 20, 1990, discloses the crystalline hydrochloride and hydrobromide salts of the cephalosporin antibiotic, ceftiofur. It discloses a variety of dosage forms, such as oral (e.g., capsules, tablets), topical, rectal (e.g., suppositories) and injectable preparations, as well as a variety of routes of administration, such as oral, intramuscular and intravenous. In fact, the product, EXCENEL® Sterile Suspension (having ceftiofur hydrochloride as its active ingredient), is currently marketed in the U.S. as a ready-to-use oil suspension product for the treatment/control of swine bacterial respiratory disease and is administered by intramuscular injection. These intramuscular injections are administered exclusively in edible tissues of the food-producing animals, namely the neck (often using the base of the ear as a landmark but not using the ear specifically as a site of injection), hindleg, and flank of the animal.

Labeeuw et al., Cephalosporin Derivatives, Process for Preparation Thereof and Drugs Containing Said Derivatives Usable as Antibiotics, U.S. Pat. No. 4,464,367, Aug. 7, 1984, discloses the cephalosporin antibiotic, ceftiofur, as well as alkali, alkaline earth and amine salts thereof. In fact, the product, NAXCEL/EXCENEL® Sterile Powder (having ceftiofur sodium as its active ingredient) is also currently marketed throughout the world for the treatment/control of bovine and swine bacterial respiratory diseases. This product must be reconstituted with sterile water before it is injected intramuscularly into cattle or swine. Once again, these injections are made into edible tissues including the neck, foreleg or hindleg, and flank of the animal.

It is known in the art to use ear tags for identification and/or for pest control in animals, such as cattle. For example: U.S. Pat. No. 4,506,630 discloses an ear tag attached to which is a vial containing, for example, a pesticide or insect repellant. U.S. Pat. No. 4,631,231 discloses pyrethroid-containing mouldings, preferably ear tags, for combating ectoparasites, e.g., flies, mites or ticks, on animals, especially cattle. U.S. Pat. No. 4,495,898 discloses a pest control device for animals composed of an identification tag to be attached to the animal, especially the ear, and a reservoir of insecticide.

Several solid hormonal implants (i.e., implantable pellets) for increased weight gain and feed efficiency are marketed, with the approval of the Food and Drug Administration (FDA) —Center for Veterinary Medicine (CVM), as over-the-counter products, not requiring the order of or the supervision of a veterinarian, such as the following: IMPLUS-H® Heifer Implants and IMPLUS-S® Steer Implants (Ivy Labs); SYNOVEX®C Calf Implants, SYNOVEX®H Heifer Implants and SYNOVEX®S Steer Implants (Syntex); COMPUDOSE® 200 Estradiol (Elanco); RALGRO® Beef Cattle Implants and RALGRO® Feedlot Lamb Implants (Malinkrodt); REVALOR®-S For Feedlot Steers, FINAPLIX®-H For Feedlot Heifers and FINAPLIX®-S For Feedlot Steers (Hoechst Roussel). The ear is a common place for administration of approved OTC implants. For example, French Pat. No. FR2239988 discloses animal hormone implants for use especially behind the ear. U.S. Pat. No. 3,428,729 discloses a controlled release medicament, such as a hormone, especially for subcutaneous ear implants in animals.

Japanese Pat. No. J59181208 published Oct. 15, 1984 discloses a pharmaceutical-containing adhesive formulation for external application having a pharmaceutical in an adhesive base and used, for example, to apply to the auricle (i.e., the earlobe) of the ear. These transdermal devices, which are bent to attach to both sides of the earlobe, are adhered to the stratum corneum of the ear (i.e., the surface of the ear), a location chosen most likely to maximize adhesion and minimize removal of the device by the animal.

"Microchip Implant Sites Identified by USDA," Feedstuffs, Sept. 30, 1996, page 6, reports that the Food & Drug Administration has given clearance for the implanting of microchips in food animals, clearing the way for the Destron Fearing Corp. to market its electronic identification (EID) products to the livestock industry. The four implantation sites that were identified in an animal, all sites being inedible tissue, were as follows: (1) subcutaneous on the scutiform cartilage at the base of the ear; (2) subcutaneous above the dewclaw of the foot; (3) subcutaneous in the infraorbital fossa in swine; and (4) in the ligamentum nuchae in horses.

T. G. Watson, B. C. Hosking and F. G. Hooke, "Efficacy of Doramectin Against Experimental Infections by Some Nematode Parasites in Cattle in New Zealand," New Zealand Veterinary Journal, vol. 43, no. 2, pages 67–69 (1995), studied the efficacy of the novel avermectin, doramectin, against experimental larval and adult infections of three species of nematode parasites important to cattle production in New Zealand. Given as a single subcutaneous injection behind the ear (as a landmark), doramectin was very effective against the parasite when compared to infections established in untreated controls. In M. McHardy and D. W. T. Morgan, "Treatment of *Theileria annulata* Infection in Calves with Paraquone," Research in Veterinary Science, vol. 39, no. 1, pages 1–4 (1985), calves were infected with this parasite by subcutaneous injection in front of the right ear (once again, as a landmark). Particular groups of the calves were treated by intramuscular injection on the right side of the neck with parvaquone, resulting in certain animals being clinically cured.

P. Houpert et al., "Intra- vs Intermuscular Injections in Swine," Veterinary Research, vol. 24, no. 3, pages 278–285 (1993), determined the exact localization (intra- or intermuscular) of a drug administered by a so-called intramuscular technique. It concluded that an injection in the neck (perpendicular to the skin surface using the landmark of just behind the base of the ear) was the most appropriate site for intramuscular injection in pigs. F. B. Bilalov, "Haematological and Immunomorphological Investigation of Pigs Given Swine Erysipelas Vaccine as a Single Intramuscular Deposit or by Tissue Infiltration," Diagnosis of Infectious Diseases of Farm Animals," (Russian) pages 132–135 (1982), ten pigs were given a single intramuscular injection of 1 ml of the VR2 (BP2) attenuated strain of *Erysipelothris rhusiopathiae*, in the conventional way, into the neck 10 cm from the ear. I. Rumachik, I. Soloneko and P. E. Sakhonchik, "Effectiveness of Tuberculin Testing in Pigs at Various Sites on the Body," Veterinarnaya Nauka—Proizvodstvu (Russian), vol. 26, pages 36–44 (1988), found that intradermal injection of a small volume (approximately 0.1 to 0.5 mL) of the tuberculin antigen in the skin of the ear flaps of pigs gave more reliable results than injection into the neck or lumbar region. I. Genov, V. Tsutsumanski and K. H. Lalov, "Trial to Obtain and Use Allergen in Animal Leukosis Diagnostics," Vet. Med. Nauki, Vol. 17(2) pages 42–47 (1980, Recd. 1981), found that the most suitable site to inject the allergen proved to be the tail fold for cattle and sheep and the dorsal part of the ear near the medial line for pigs. The allergen reaction may be used for quick herd diagnosis of leukosis. Once again, this is a nontherapeutic diagnostic test using a small volume (approximately 0.1 to 0.5 mL) of an antigen injected intradermally, at the base of the ear of swine, to allow visualization of the local tissue reaction (similar to tuberculin testing in humans). P. D. McKercher and H. L. Bachrach, "A Foot-and-Mouth Disease Vaccine for Swine," Can. J. Comp. Med., vol. 40(1), pages 67–74 (1976), found that significant protection against this disease was afforded when small volumes (0.1 to 0.5 mL) of disease-preventing vaccine were applied with a jet injector gun to the ear (intradermally and intramuscularly in the dorsal part of the ear) or neck of swine. In other experiments, the vaccine was administered prophylactically subcutaneously by hypodermic syringe to the dorsal part of the ear, and was administered subcutaneously by injection gun to the posterior side of the ear to check for tissue reactions. The latter is a biological agent (i.e., vaccine) administered in small volume rather than a pharmaceutical agent administered in relatively large volume (1 to 15 mL) as in the present invention. Th. Alogninouwa et al., "Comparative Efficacy of Ivermectin and Deltamethrin in the Treatment of Porcine Scabies," Revue de Medecine Veterinaire, vol. 144, no. 7, pages 599–605 (1993), discusses the efficacy of ivermectin in comparison to another antiparasitic in swine. Ivermectin was administered by subcutaneous injection at the base of the ear, not in the ear. In this method of administration, the ear is used as a landmark and the injection is made in the pig's neck just caudal to (i.e., behind) the base of the ear, within a couple of centimeters. The injection site remains on the carcass when the ears are removed. In the present invention, where the drug is administered subcutaneously in the posterior side of the auricle of the ear, the injection site remains with the ear upon its removal at the slaughterhouse.

M. A. Koutchoukali et al., "Primary Vaccination Against Rabies in the Dog by the Intradermal Route: Comparison of its Effectiveness Depending on the Site of the Injection: Ear or Thigh," Revue de Medecine Veterinarie, vol. 136, no. 7, pages 505–508 (1985); B. Toma et al., "Vaccination in the Dog Against Rabies: Serological Response Compared One Year After Vaccination by the Intradermal or Subcutaneous Route," Recueil de Medecine Veterinaire, vol. 159, no. 7, pages 645–652 (1983); describe vaccination of dogs for rabies by intradermal injection in the internal surface of the ear, in comparison to subcutaneous administration in the lateral flank and to the rear leg. These references focused on intradermal versus subcutaneous administration with secondary emphasis on the location of administration. Intradermal administration in the ear of the vaccines worked better than the other methods of administration with regard to maintenance of titers.

R. F. Borgman et al., "Ear Lesions Produced in Rabbits by Sterol Injections," American Journal of Veterinary Research, vol. 33, no. 11, pages 2309–2315 (1972), studied ear lesions induced in rabbits as a model for atherosclerosis. Lesions were produced when cholesterol, cholesterol esters and similar compounds were intradermally injected into the auricles (i.e., flaps) of rabbit ears.

As demonstrated by the above references, the administration by injection of an antimicrobial sterile suspension formulation (e.g., ceftiofur crystalline free acid sterile suspension) subcutaneously (SC) in the neck, flank, or other subcutaneous sites on the carcass for the treatment of bacterial diseases, such as bovine respiratory disease (BRD) and swine respiratory disease (SRD) is known. The subcutaneous aural (i.e., ear) administration of hormones as solid dose implants is known. Implants of antibiotics are known but are typically administered intramuscularly in the edible tissues of the food-producing animal, not in the ear. Small-volume vaccines have been administered successfully intradermally in the ear of dogs and swine. Also in swine, diagnostic allergens and a vaccine in small volumes have been administered subcutaneously in the dorsal part or the posterior side of the ear.

However, the aural administration of an antibiotic injected subcutaneously in the posterior side of the auricle of the ear of cattle or swine is novel. More specifically, the aural administration of an antimicrobial sterile suspension injected subcutaneously in the posterior ear is novel. Certainly, none of these references disclose the ear as the preferred route of administration for a pharmaceutical compound, and specifically an antimicrobial agent. No antimicrobial, or, more specifically, no variable dose formulation of an antimicrobial, is disclosed as being administrated in the ear.

Furthermore, the administration in the ear, according to the present invention, resulted in unexpected results in the properties/performance of the antimicrobial suspension. As will be described further below, it was observed that the subcutaneous aural administration of an antimicrobial sterile suspension provided comparable systemic plasma concentrations of active drug, and slightly faster absorption, relative to subcutaneous administration in the neck.

SUMMARY OF THE INVENTION

The present invention particularly provides:

A method of administering an amount of an antibiotic effective to treat or prevent a bacterial infection in an animal in need thereof which comprises:

injecting the antibiotic subcutaneously in the posterior of the ear of the animal.

More particularly, the present invention provides:

This method wherein the antibiotic is selected from the group consisting of: procaine penicillin, benzathine penicillin, ceftiofur crystalline free acid, ceftiofur hydrochloride, ampicillin trihydrate, amoxicillin trihydrate, oxytetracycline, erythromycin, tylosin, tilmicosin, florfenicol, enrofloxacin, danofloxacin and premafloxacin;

This method wherein the animal is selected from the group consisting of: cattle, swine, sheep and goats;

This method wherein the antibiotic is in a formulation;

This method wherein the formulation is a sterile oil suspension;

This method wherein the volume of the formulation is from about one (1) to about fifteen (15) ml;

This method wherein the antibiotic is injected in the middle third of the posterior of the ear of the animal;

This method of claim 1 wherein prior to administration the ear is folded in half along the long axis so that the top border of the ear touches the bottom border;

This method wherein the antibiotic is injected approximately midway from the base to the tip of the ear and approximately one-half (½) to one (1) inch from the top edge of the ear;

This method wherein the antibiotic is injected with a single syringe needle;

Most particularly, the present invention provides:

This method wherein the antibiotic is crystalline ceftiofur free acid of formula I as shown below;

This method wherein the ceftiofur crystalline free acid is in a sterile oil suspension;

This method wherein the bacterial infection is bovine respiratory disease or swine respiratory disease;

This method wherein the amount of ceftiofur crystalline free acid is from about 1.1 to about 8.8 mg/kg of body weight; and This method wherein the amount of ceftiofur crystalline free acid is from about 4.4 to about 6.6 mg/kg of body weight.

Ceftiofur crystalline free acid (CCFA) has the following formula I:

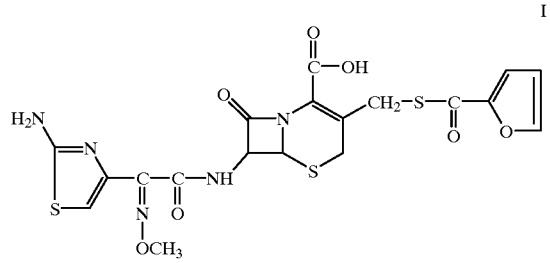

It is the crystalline form of the compound commonly known as ceftiofur, which is more properly named 7-[2-(2-amino-1,3-thiazol-4-yl)-2-methoxyimino) acetamido]-3-

[(fur-2-ylcarbonyl)thiomethyl]-3-cephem-4-carboxylic acid (also named as 7-[2-(2-amino-4-thiazolyl)-2-(methoxyimino)acetamidol]-3-[(2-furanylcarbonyl)thiomethyl)-8-oxo-5-thia-1-azabicyclo[4.2.0]oct-2-ene-1-carboxylic acid. CCFA, as well as formulations containing it, are described and prepared (especially at pages 8–14) in the International Publication No. WO 94/20505, which was published Sept. 15, 1994, which is incorporated by reference herein.

Ceftiofur crystalline free acid sterile oil suspension (CCFA-SS) (100 mg/ml and 200 mg/ml) is a sustained-release ceftiofur formulation that provides for prolonged absorption from the injection site and thus affords a single injection treatment of bacterial diseases in animals. CCFA-SS will be a prescription product for use in cattle for the treatment of the bacterial component of bovine respiratory disease associated with microorganisms susceptible to ceftiofur, such as *Pasteurella haemolytica, Pasteurella multicida* and *Haemophilus somnus*. In addition, CCFA-SS will be a prescription product for use in swine for the treatment of the bacterial component of swine respiratory disease associated with microorganisms susceptible to ceftiofur, such as *Actinobacillus pleuropneumoniae, Streptococcus suis* and *S. parasuis*, and *P. multocida*.

Other antibacterial agents can be administered according to the method of the present invention. These injectable antibiotics include the following: injectable suspensions of sparingly water-soluble antimicrobial agents, such as procaine penicillin, benzathine penicillin, ceftiofur crystalline free acid (CCFA), ceftiofur hydrochloride, ampicillin trihydrate and amoxicillin trihydrate; sustained-release non-aqueous solutions of sparingly water-soluble antimicrobial agents, such as oxytetracycline, erythromycin, tylosin, tilmicosin and florfenicol; and injectable solutions of zwitterionic antimicrobial agents, such as enrofloxacin, danofloxacin and premafloxacin. Amounts of these antibiotics effective to treat bacterial infections would be readily apparent to one of ordinary skill in the art. Examples of the approved forms, usages and dosages of these antibiotics, which are hereby incorporated by reference herein, appear in Veterinary Pharmaceuticals and Biologicals®, 10th edition (1997) Veterinary Medicine Publishing Group, Lenexa, Kans., (the page numbers are indicated in parentheses): procaine penicillin (pages 422, 492 and 674–75), benzathine penicillin (pages 422, 492 and 675), ceftiofur hydrochloride (pages 550–51), ampicillin trihydrate (page 684), amoxicillin trihydrate (pages 427–28), oxytetracycline (pages 617–18 and 622), erythromycin (pages 547–48), tylosin (page 773), tilmicosin (page 630), florfenicol (page 652) and enrofloxacin (pages 448–49). U.S. Pat. No. 5,563,155 (Oct. 8, 1996), which is hereby incorporated by reference herein, describes quinolone-type antibacterial agents, including premafloxacin. The effective dosage range of CCFA is 1.1 to 8.8 mg CE (ceftiofur equivalents)/kg BW (body weight) when administered SC in the posterior ear as a single injection. More preferably, the dosage range is 4.4 to 6.6 mg/kg daily. Also the present invention may be used to deliver large quantities or volumes of these antibiotic formulations, such as from one (1) to fifteen (15) ml.

The "posterior" part (which may also be referred to as the dorsal part) of the ear is the convexly curved back part of the ear. Currently, the ears of cattle are not considered edible by the United States Government according to USDA regulations.

Animals as used herein include cattle, swine, sheep and goats.

According to the present invention, all injections of antibiotics, such as CCFA-SS, are administered subcutaneously (SC) in the posterior ear. Animals will not receive an ear tag and antibiotic in the same ear. Prior to administration, the animal's head may be stabilized using a chin rest/head stabilizer on the chute or a halter.

A method of administering an antibiotic according to the present invention is described as follows: A 16 gauge ½ inch (1.25 cm) sterile needle or a 16 G1 inch (2.5 cm) sterile needle to used to administer each animal's injection. With the bevel of the needle facing away from the skin of the posterior ear, the needle will be inserted subcutaneously (SC) at the midline of the ear, in approximately the middle third of the ear as shown in FIG. 1:

After the needle is fully inserted in the ear, the thumb should be placed over the needle at the base of the needle hub and the syringe moved laterally approximately 1–2 cm to both the left and the right. The full contents of the syringe will then be delivered and the needle will be slowly withdrawn. Before releasing the ear, direct pressure will be applied to the injection hole as required to stop any backflow of the injected material. Following use, needles will be placed in an appropriate container for safe and appropriate disposal.

A preferred method of administering an antibiotic according to the present invention is described as follows: A 16 gauge ¾ inch (1.25 cm) sterile needle or a 16 G 1 inch (2.5 cm) sterile needle attached to an eccentric hub syringe will be used to administer each animal's injection. The hand not holding the syringe will be used to grasp the ear and fold it approximately in half along the long axis (i.e., proximal to distal; like a taco shell) so that the top (caudal) border of the ear almost touches the bottom (rostral) border. The point of needle insertion will be approximately midway from the base of the ear to the tip of the ear, and approximately ½ to 1 inch from the top edge of the ear. The hub of the syringe will be placed against the skin of the ear so that the bevel of the needle is facing up (away from the skin before the needle is inserted) with the needle pointing towards the base of the ear. Once the needle is fully inserted, the drug administrator will draw back on the syringe plunger to assure that the needle is not in a blood vessel and has not penetrated the skin. If the needle comes out through the skin while being inserted, the needle will be withdrawn and reinserted near the point where it came out through the skin. This will reduce backflow through the extra hole. Once the drug administrator is assured that the needle placement is appropriate, the full contents of the syringe will be discharged. While the syringe contents are being delivered, the thumb of the hand holding the ear will be placed across the needle at the needle insertion hole and pressure will be applied on the ear against the index finger. This will help force the injected material towards the base of the ear and away from the needle insertion hole. Following complete delivery the needle will be removed and the thumb will remain over the needle insertion hole. The thumb will apply pressure on the ear against the index finger. The other hand will be used to gently massage the injected material toward the base of the ear (away from the needle insertion hole). Pressure will be applied by the thumb to the needle insertion hole as required to minimize backflow of injected material. Following use, needles will be placed in an appropriate container for safe and appropriate disposal. FIG. 2 provides a visual representation of the technique used.

Needle injection is the preferred method of delivery, although use of syringes, automatic syringes, repeat-dose syringes, and injection guns can also be used in a similar manner, which would be readily known to one of ordinary skill in the art.

Injection of CCFA subcutaneously in the ear of cattle provides for sustained release of the drug from an injection site that is not an edible tissue and therefore, will not be of any human food safety concern. Thus, other tissues may be used as the target tissue, using the concentrations in those tissues that is deemed to be safe from toxicological studies and food consumption factors. Using this scenario, CCFA may indeed have a zero-day slaughter withdrawal time, because the residues in all edible tissues are below the safe concentrations determined for each tissue by FDA/CVM by the earliest possible slaughter time. This is a great advantage from a customer standpoint because it is not necessary to wait an extended period to slaughter the animals. Furthermore, it provides significant consumer safety attributes because the locus of substantial drug residues from sustained-release injectable products, namely the injection site, resides in an tissue that is not consumed by human beings.

When ceftiofur crystalline free acid is administered to cattle using the ear as the location for injection, plasma concentrations are therapeutic and sustained above the minimum inhibitory concentration (MIC) for the bacteria responsible for bovine respiratory disease for greater than 120 hours (5 days) at doses of 5.5 mg/kg. The finding that the time concentrations remain above the MIC after injection in the ear is similar to that achieved with CCFA after subcutaneous administration in the neck.

In addition, peak plasma concentrations after aural (ear) injection are higher and are achieved more quickly than peak concentrations after subcutaneous injection in the neck. This is unexpected, as the limited blood flow to and from the ear was expected to prolong absorption from that site with respect to the subcutaneous injection in the neck, and probably limit the relative bioavailability to a small fraction of the subcutaneous bioavailability.

Evaluation of the relative bioavailability of CCFA from the ear is approximately 65–75% compared with the systemic availability of CCFA after subcutaneous administration in the neck. This high relative bioavailability and rapid peak concentrations were unexpected, as hormones currently administered in the ear of cattle are designed for very prolonged release over several months, without discernable "peak" concentrations achieved (but rather "steady-state" concentrations achieved).

It has also been found that CCFA administered subcutaneously (SC) in the posterior of the ear provided similar plasma disposition but was not bioequivalent (as defined classically by one of ordinary skill in the art) to CCFA administered in the cervical neck. Administration of CCFA subcutaneously in the posterior ear resulted in slightly shorter time to detectable plasma concentrations of ceftiofur and metabolites and slightly higher peak concentrations than when CCFA was administered SC in the cervical neck. Furthermore, it provided total systemic exposure, as defined by the area under the plasma concentration versus time curve, that was not different from subcutaneous administration of the same dose of CCFA in the cervical neck. In addition, absorption from the posterior ear was prolonged in a similar manner to, but slightly more rapid than, subcutaneous administration in the cervical neck. Administration of CCFA sterile suspension in the posterior ear using concentrations of either 100 mg ceftiofur equivalents/mL of formulation or 200 mg ceftiofur equivalents/mL of formulation resulted in similar plasma concentrations over time after administration. Furthermore, similar doses of CCFA sterile suspension are effective in the treatment of bovine respiratory disease after subcutaneous administration in the cervical neck and after subcutaneous administration in the convex posterior ear.

Residue studies from cattle administered CCFA in the posterior of the ear indicated that, once the ear is removed from the carcass and is disposed as inedible trim, the remaining carcass, 12 hours after administration, does not contain a locus of drug residues near the injection site (i.e., at the base of the ear) that poses a human health hazard upon consumption of the edible tissues of the animal.

CCFA may also be administered SC in the posterior ear either at arrival processing or for the treatment of BRD (usually early in the feedlot stay) in combination with growth-promoting steroid implants administered in approximately the same location and time at arrival processing. Studies have shown that concurrent administration of CCFA sterile suspension and growth-promoting hormonal implants in the same ear of cattle did not adversely effect the efficacy of the hormonal implants as indicated by rate of growth and feed efficiency of the treated cattle compared with untreated controls and cattle treated only with the hormonal implants.

Similar advantages and results are expected from the use of the method of the present invention to administer CCFA and other antibiotics to animals in need thereof, as fully described above.

DESCRIPTION OF THE PREFERRED EMBODIMENTS

EXAMPLE 1 CEFTIOFUR CRYSTALLINE FREE ACID STERILE SUSPENSION (100 or 50 mL vials, 100 or 200 mg/mL)
Formulation per mL:
Ceftiofur free acid, micronized, 100 or 200 mg/mL
Phospholipon 90-H, 0.50 mg/mL
Sorbitan monooleate NF, 1.50 mg/mL
Cottonseed oil NF, q.s. ad The procedure for the preparation of ceftiofur free acid is found in the International Publication No. WO 94/20505 (published Sept. 15, 1994), which is hereby incorporated by reference herein. The above formulation, wherein the other starting materials are commercially available, is prepared by procedures readily known to one of ordinary skill in the formulation art, and is sterilized by standard methods, such as terminal gamma irradiation.

Figure 1:
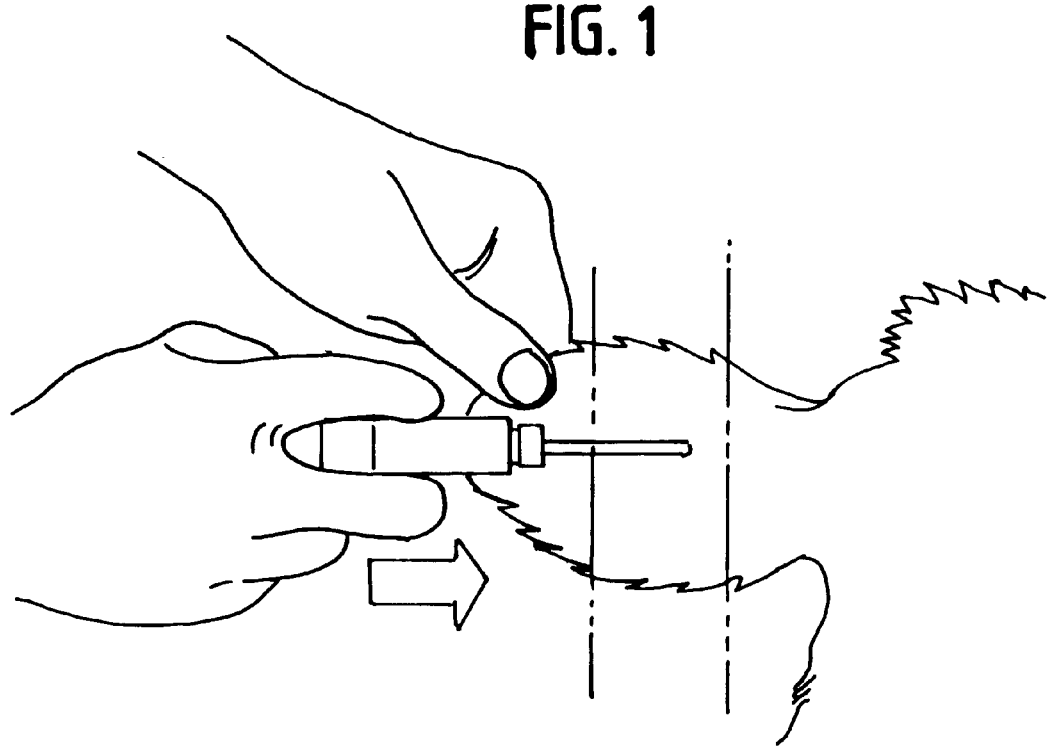
FIG. 1 shows the needle being inserted at the midline of the ear in approximately the middle third of the ear.
Figure 2:
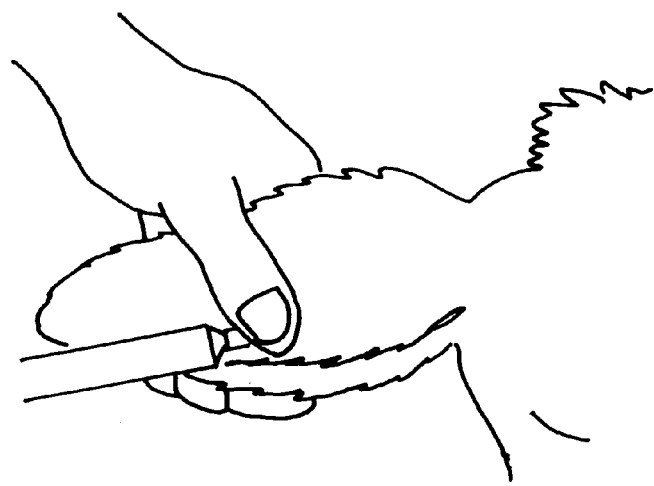
FIG. 2. provides a visual representation of a preferred method of administering an antibiotic according to the present invention.

I claim:

1. A method of administering an amount of an antibiotic effective to treat or prevent a bacterial infection in an animal in need thereof which comprises:

injecting the antibiotic, in liquid form, subcutaneously in the posterior of the ear of the animal.

2. The method of claim 1 wherein the antibiotic is selected from the group consisting of: procaine penicillin, benzathine penicillin, ceftiofur crystalline free acid, ceftiofur hydrochloride, ampicillin trihydrate, amoxicillin trihydrate, oxytetracycline, erythromycin, tylosin, tilmicosin, florfenicol, enrofloxacin, danofloxacin and premafloxacin.

3. The method of claim 1 wherein the animal is selected from the group consisting of: cattle, swine, sheep and goats.

4. The method of claim 1 wherein the antibiotic is in a formulation.

5. The method of claim 4 wherein the formulation is a sterile oil suspension.

6. The method of claim 5 wherein the volume of the formulation is from about one (1) to about fifteen (15) ml.

7. The method of claim 1 wherein the antibiotic is injected in the middle third of the posterior of the ear of the animal.

8. The method of claim 1 wherein prior to administration the ear is folded in half along the long axis so that the top border of the ear touches the bottom border.

9. The method of claim 1 or 8 wherein the antibiotic is injected approximately midway from the base to the tip of the ear and approximately one-half (½) to one (1) inch from the top edge of the ear.

10. The method of claim 1 wherein the antibiotic is injected with a single syringe needle.

11. The method of claim 2 wherein the antibiotic is crystalline ceftiofur free acid formula I

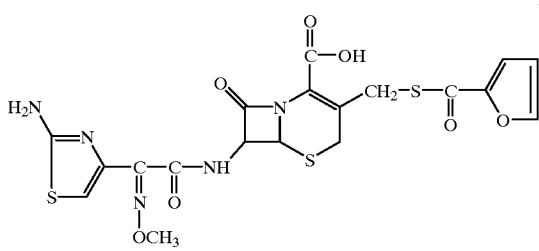

which is 7-[2-(2-amino-1,3-thiazol-4-yl)-2-methoxyimino) acetamido]-3-[(fur-2-ylcarbonyl)thiomethyl]-3-cephem-4-carboxylic acid.

12. The method of claim 11 wherein the ceftiofur crystalline free acid is in a sterile oil suspension.

13. The method of claim 12 wherein the bacterial infection is bovine respiratory disease or swine respiratory disease.

14. The method of claim 13 wherein the amount of ceftiofur crystalline free acid is from about 1.1 to about 8.8 mg/kg of body weight.

15. The method of claim 14 wherein the amount of ceftiofur crystalline free acid is from about 4.4 to about 6.6 mg/kg of body weight.

16. The method of claim 1, wherein said antibiotic is in the form of an injectable solution or injectable suspension.

* * * * *